US010842585B2

United States Patent
Mitani et al.

(10) Patent No.: US 10,842,585 B2
(45) Date of Patent: Nov. 24, 2020

(54) MODEL, MANUFACTURING SYSTEM, INFORMATION PROCESSING DEVICE, MANUFACTURING METHOD, INFORMATION PROCESSING METHOD, PROGRAM, AND RECORDING MEDIUM

(71) Applicants: UNIVERSITY OF TSUKUBA, Tsukuba (JP); DAI NIPPON PRINTING CO., LTD., Tokyo (JP)

(72) Inventors: Jun Mitani, Tsukuba (JP); Nobuhiro Ohkohchi, Tsukuba (JP); Yukio Oshiro, Tsukuba (JP); Kentaro Ko, Kawasaki (JP); Takuji Hayashi, Tsukuba (JP)

(73) Assignees: UNIVERSITY OF TSUKUBA, Tsukuba (JP); DAI NIPPON PRINTING CO., LTD., Tokyo (JP)

( * ) Notice: Subject to any disclaimer, the term of this patent is extended or adjusted under 35 U.S.C. 154(b) by 264 days.

(21) Appl. No.: 15/557,237

(22) PCT Filed: Feb. 22, 2016

(86) PCT No.: PCT/JP2016/055049
§ 371 (c)(1),
(2) Date: Sep. 11, 2017

(87) PCT Pub. No.: WO2016/152356
PCT Pub. Date: Sep. 29, 2016

(65) Prior Publication Data
US 2018/0049838 A1    Feb. 22, 2018

(30) Foreign Application Priority Data
Mar. 24, 2015    (JP) .................................. 2015-060937

(51) Int. Cl.
*A61B 90/00* (2016.01)
*G09B 23/30* (2006.01)
(Continued)

(52) U.S. Cl.
CPC .............. *A61B 90/08* (2016.02); *B29C 64/10* (2017.08); *B29C 67/00* (2013.01); *B33Y 10/00* (2014.12);
(Continued)

(58) Field of Classification Search
CPC ... A61B 2034/105; A61B 90/08; B29C 64/10; B29C 64/112; B29C 64/386;
(Continued)

(56) References Cited

U.S. PATENT DOCUMENTS

2014/0017651 A1    1/2014  Sugimoto et al.
2015/0029184 A1*   1/2015  Masumoto .............. G06T 19/00
                                                    345/419

(Continued)

FOREIGN PATENT DOCUMENTS

JP    H05-011689 A    1/1993
JP    2014-176425 A   9/2014
(Continued)

OTHER PUBLICATIONS

S130-2, Kanzo no Kekkan Bunpu Mokei, Seiri Kaibo Mokei, Sakamoto Model Corporation , May 2016, p. 31.
(Continued)

*Primary Examiner* — Vincent H Tran
(74) *Attorney, Agent, or Firm* — Oliff PLC

(57) ABSTRACT

A model of a body part, e.g., liver, of which the internal structure can be observed easily; and others. In a liver model according to the present invention, the liver parenchyma is formed in the form of a frame to make it possible to observe the portal, veins, a tumor and others in the inside of the
(Continued)

frame 31a easily. In addition, the liver model can be handled easily by gripping a gripping part provided at the lower end surface of the inferior vena cava, and the tumor is integrated with the liver model by means of a joint part. The liver model can be manufactured from a model material using a 3D printer on the basis of three-dimensional shape data for model manufacturing purposes, which are produced using an information processing device.

16 Claims, 13 Drawing Sheets

(51) Int. Cl.
| | |
|---|---|
| B33Y 50/00 | (2015.01) |
| B29C 67/00 | (2017.01) |
| B33Y 10/00 | (2015.01) |
| B33Y 30/00 | (2015.01) |
| B29C 64/10 | (2017.01) |
| B29C 64/386 | (2017.01) |
| A61B 34/10 | (2016.01) |
| B29C 64/112 | (2017.01) |
| B33Y 80/00 | (2015.01) |

(52) U.S. Cl.
CPC ............... *B33Y 30/00* (2014.12); *B33Y 50/00* (2014.12); *G09B 23/30* (2013.01); *A61B 2034/105* (2016.02); *B29C 64/112* (2017.08); *B29C 64/386* (2017.08); *B33Y 80/00* (2014.12)

(58) Field of Classification Search
CPC ......... B29C 67/00; B33Y 10/00; B33Y 30/00; B33Y 50/00; B33Y 80/00; G06F 17/50; G09B 23/30
See application file for complete search history.

(56) References Cited

U.S. PATENT DOCUMENTS

| | | | | |
|---|---|---|---|---|
| 2015/0145171 | A1* | 5/2015 | Walker | B33Y 10/00 264/401 |
| 2016/0096318 | A1* | 4/2016 | Bickel | B33Y 30/00 264/40.1 |

FOREIGN PATENT DOCUMENTS

| | | |
|---|---|---|
| JP | 2015-506002 A | 2/2015 |
| WO | 2012/132463 A1 | 10/2012 |

OTHER PUBLICATIONS

S130-2 Kanzo no Kekkan Bunpu Mokei, Medical Online, Apr. 21, 2016, <URL: http://dev.medicalonline.jp/index/product/eid/44680. (Physiological Anatomical Models).
May 10, 2016 Search Report issued in International Patent Application No. PCT/JP2016/055049.
Sep. 26, 2017 International Preliminary Report on Patentability issued in International Application No. PCT/JP2016/055049.
Feb. 12, 2020 Office Action issued in Japanese Patent Application No. 2017-507619.
Kensaku Mori; "Organ Model Fabrication by Medical Image Processing and 3D Printer and Its Application to Diagnostic and Surgical Aid;" Information and Communication, Nagoya University; pp. 2-5; 2015.

* cited by examiner

Fig. 6
(a)
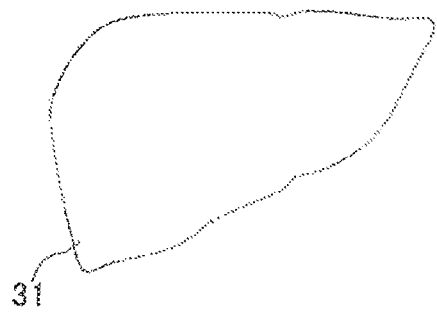
(b)
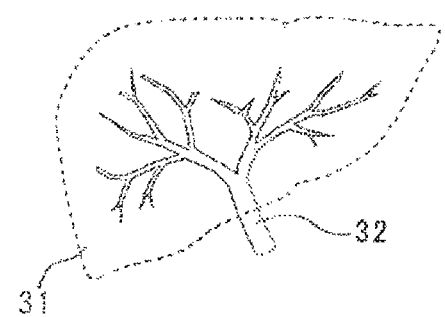
(c)
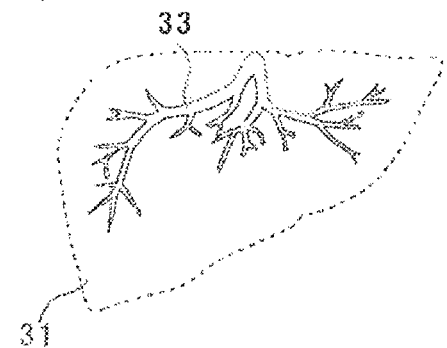
(d)
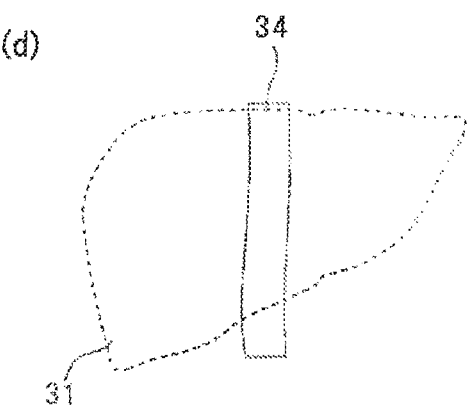
(e)
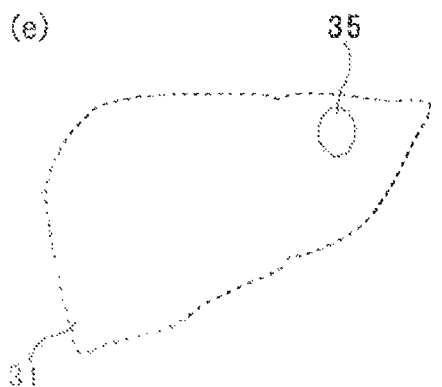

MODEL, MANUFACTURING SYSTEM, INFORMATION PROCESSING DEVICE, MANUFACTURING METHOD, INFORMATION PROCESSING METHOD, PROGRAM, AND RECORDING MEDIUM

TECHNICAL FIELD OF THE INVENTION

This invention relates to a model and a manufacturing system thereof, an information processing device, a manufacturing method, an information processing method, a program, and a recording medium.

BACKGROUND OF THE INVENTION

In recent years, many attempts have been made to manufacture various articles with solid modeling techniques using 3D printers and the like. The medical field is no exception and Patent Document 1 discloses a method for manufacturing a liver model used for operation plans or informed consent and so on.

RELATED ART

Patent Documents

[Patent Document 1] Japanese Unexamined Patent Application Publication No. H5-11689 (JP-A-H5-11689)

SUMMARY OF THE INVENTION

Problems to be Solved by the Invention

A conventional liver model made by a 3D printer has a solid liver parenchyma, which contains the structural parts such as blood vessels like a portal and veins, or tumors therein. However, depending on the shape of the liver parenchyma or conditions of the surface of the model, there has been a problem that the blood vessels or the tumors in the liver parenchyma may appear to be distorted or indistinct. In addition, the conventional method uses a lot of costly model material for forming the liver parenchyma, which leads to a problem of high manufacturing costs.

The present invention was made in view of above problems. Its object is to provide a model of a body part, such as a liver, of which the internal structure can be easily observed, and the like.

Means for Solving Problems

To achieve the above object, a first invention is a model that imitates a body part and includes a frame and a body structural part that are formed from a forming material. The frame is formed along at least a part of an outer surface of the body part, and at least a part of the body structural part is inside the body part.

It is preferable that the model includes a joint part that joins the body structural part to the other body structural part or the frame. Also, the model preferably includes a gripping part for gripping the model. The body part is, for example, a liver. Furthermore, the model may be manufactured for a part of the body part.

In the model imitating the body part of the present invention, the body part is represented as a hollow frame structure so body structural parts such as blood vessels and tumors inside the body part can be observed easily. Thus, the model is suitable to be used as reference in operation planning or in consultation with patients for informed consent, or to be used for operations, education and so on. Also, the amount of expensive model materials used for making the model is reduced, which reduces the costs, so the present invention can be spread widely not only in the researching field but also in the clinical sites. It should be noted that a body part refers widely to a part of a human or an animal body such as an organ, e.g. a liver, or a muscle. Also, a body structural part refers widely to a structural part, such as a blood vessel and a nerve, associated with the body part.

Also in the present invention, the body structural part such as the tumor is joined to another body structural part or the frame by a means of the joint part so that the body structural part such as the tumor may not fall off from the model. Moreover, providing the gripping part for gripping the model facilitates handling of the model. Also, it is possible to manufacture a model for a part of a body part as necessary, allowing the model to be downsized.

A second invention is a manufacturing system of a model imitating a body part. The manufacturing system includes an information processing device and a 3D printer. The information processing device records three-dimensional shape data for the body part and three-dimensional shape data for a body structural part, at least a part of which is inside the body part, and generates three-dimensional shape data for a frame that is formed along at least a part of an outer surface of the body part. The 3D printer forms three-dimensional shapes of the frame and the body structural part corresponding to the three-dimensional shape data for the frame and the body structural part from a forming material.

Preferably, the information processing device generates three-dimensional shape data for a joint part that joins the body structural part to the other body structural part or the frame, and the 3D printer forms a three-dimensional shape of the joint part corresponding to the three-dimensional shape data for the joint part from a forming material. Also, the information processing device preferably generates three-dimensional shape data for a gripping part for gripping the model, and the 3D printer forms a three-dimensional shape of the gripping part corresponding to the three-dimensional shape data for the gripping part from a forming material. The body part is a liver, for example.

A third invention is an information processing device that generates three-dimensional shape data for a body part to be used in manufacturing a model imitating the body part using a 3D printer. The information processing device records three-dimensional shape data for the body part and then generates three-dimensional shape data for a frame that is formed along at least a part of an outer surface of the body part from the three-dimensional shape data for the body part.

Preferably, the information processing device of the third invention further records three-dimensional shape data for a body structural part, at least a part of which is inside the body part, and generates three-dimensional shape data for a joint part that joins the body structural part to the other body structural part or the frame. Also, it is preferable that three-dimensional shape data for a gripping part for gripping the model is generated. The body part is a liver, for example.

A fourth invention is a manufacturing method for a model imitating a body part using an information processing device and a 3D printer. The information processing device, which records three-dimensional shape data for the body part and three-dimensional shape data for a body structural part, at least a part of which is inside the body part, generates three-dimensional shape data for a frame that is formed along at least a part of an outer surface of the body part from the three-dimensional shape data for the body part. The 3D printer forms three-dimensional shapes of the frame and the body structural part corresponding to the three-dimensional shape data for the frame and the body structural part from a forming material.

A fifth invention is an information processing method that generates three-dimensional shape data to be used in manufacturing a model imitating a body part using a 3D printer. The information processing device generates three-dimensional shape data for a frame that is formed along at least a part of an outer surface of the body part from the three-dimensional shape data for the body part.

A sixth invention is a program that operates a computer as an information processing device that generates three-dimensional shape data to be used in manufacturing a model imitating a body part using a 3D printer. The information processing device generates three-dimensional shape data for a frame that is formed along at least a part of an outer surface of the body part from the three-dimensional shape data for the body part.

A seventh invention is a recording medium that records a program that operates a computer as an information processing device that generates three-dimensional shape data to be used in manufacturing a model imitating a body part using a 3D printer. The information processing device generates three-dimensional shape data for a frame that is formed along at least a part of an outer surface of the body part from the three-dimensional shape data for the body part.

Effects of the Invention

The present invention can provide a model of a body part, such as a liver, of which the internal structure can be easily observed, and the like.

BRIEF DESCRIPTION OF DRAWINGS

FIG. 5 is a drawing showing three-dimensional shape data for a liver parenchyma 31, a portal 32, veins 33, an inferior vena cava 34, and a tumor 35.
FIG. 13 is a drawing showing a liver model 3a.

DESCRIPTION OF SOME EMBODIMENTS

Hereinafter, some preferred embodiments of the present invention will be described in detail with reference to the accompanying drawings.

(1. Manufacturing System 1)

Figure 1:
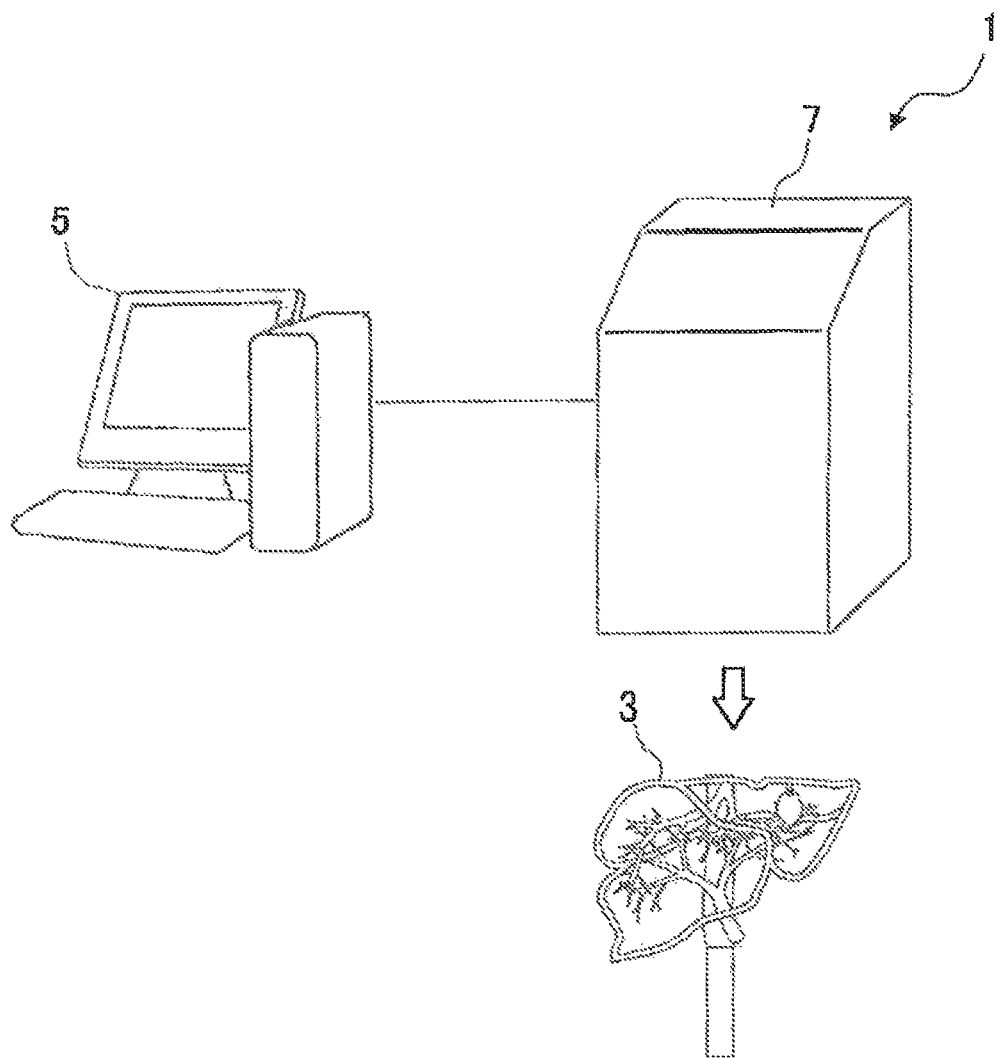
FIG. 1 is a drawing showing a manufacturing system 1.

FIG. 1 is a drawing showing a manufacturing system 1 according to an embodiment of the present invention. This manufacturing system 1 manufactures a liver model 3 and includes an information processing device 5, a 3D printer 7, and so on.

The information processing device 5 generates three-dimensional shape data for model manufacturing purposes to manufacture the liver model 3 using the 3D printer 7.

Figure 2:
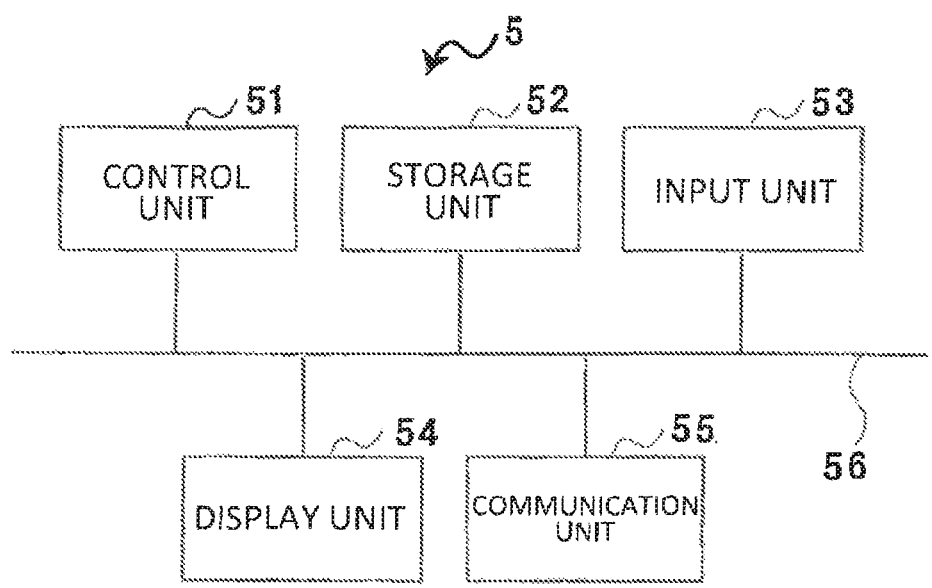
FIG. 2 is a drawing showing a hardware configuration of an information processing device 5.

FIG. 2 is a drawing showing a hardware configuration of the information processing device 5. As shown in the drawing, the information processing device 5 can be implemented with a computer in which a control unit 51, a storage unit 52, an input unit 53, a display unit 54, a communication unit 55, and the like are connected with each other via a bus 56. However, the configuration of the information processing device 5 is not limited thereto.

The control unit 51 includes CPU, ROM, RAM, and the like. CPU loads a program according to a process described below of the information processing device 5 that is stored in a recording medium such as the storage unit 52 or ROM to a working memory region on RAM, and then run the program to drive and control each part connected with each other via the bus 56 to execute the process. ROM is a non-volatile memory and holds programs, data, and the like permanently. RAM is a volatile memory temporarily holding programs, data, and the like loaded from the storage unit 52, ROM, or the like, as well as providing a working area for use of various processes executed by the control unit 51.

The storage unit 52 is a hard disc drive or the like, which stores a program to be executed by the control unit 51 and data and the like required to execute the program.

The input unit 53 provides operation and running commands to the computer or inputs data and the like to the computer, and includes an input device such as a touch panel or keys.

The display unit 54 includes a display device such as a liquid-crystal panel and a logic circuit or the like, which implements the displaying function in cooperation with the display device.

The communication unit 55 is a communication interface that acts as a medium for communication through networks or the like.

The bus 56 is a path that mediates sending and receiving of control signals, data signals and the like between each part.

The 3D printer 7 manufactures the liver model 3 based on the three-dimensional shape data for model manufacturing purposes. As the 3D printer 7, an inkjet printer may be used, for example. In the inkjet printer, a model material and a support material are applied by jet based on sliced data obtained from horizontally slicing the three-dimensional shape data for model manufacturing purposes into a plurality of layers arranged one above the other, and then the model material resin is cured by irradiating UV light thereto. This process is repeated from a bottom layer to an upper layer so as to laminate the resin. In this way, detailed shapes such as blood veins can be represented with high accuracy.

The model material is a resin used as a forming material of the liver model 3 and the support material is a resin used to support the model material from underneath. After the liver model 3 is manufactured, the support material is removed. A material that can be easily removed by washing or the like is used as the support material.

As the model material, various types of acrylic resin having a UV curable characteristic can be used. As the support material, various types of resin, such as gel-like resin that can be removed by water jet, a wax material with a low melting point that can be removed by heating, or a water soluble resin that can be removed by soaking into water, can be used.

The 3D printer 7 is not limited to the one mentioned above, and a printer using an FDM (Fused Deposition Modeling) method, in which resin is laminated by repeatedly applying a molten material from a nozzle head from the bottom layer to the upper layer based on the slice data, or the like can also be used.

(2. Liver and the Liver Model 3)

Figure 3:
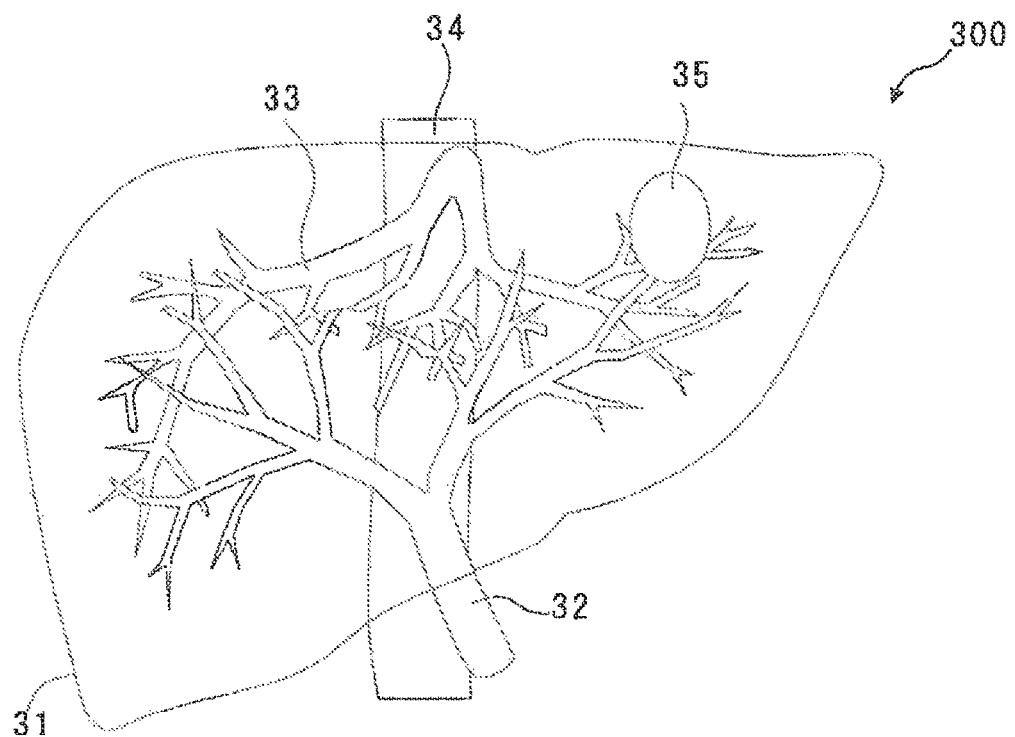
FIG. 3 is a drawing showing an example of three-dimensional shape data for a liver 300.

The liver model 3 is a model imitating a human liver. FIG. 3 is a schematic view of three-dimensional shape data for a liver 300 and includes a liver parenchyma 31, which is a main body of a liver as a body part, and a portal 32, veins 33, an inferior vena cava 34, and a tumor 35, which are body structural parts associated with the liver. Although omitted in the drawing, the body structural parts also include arteries and the like.

Figure 4:
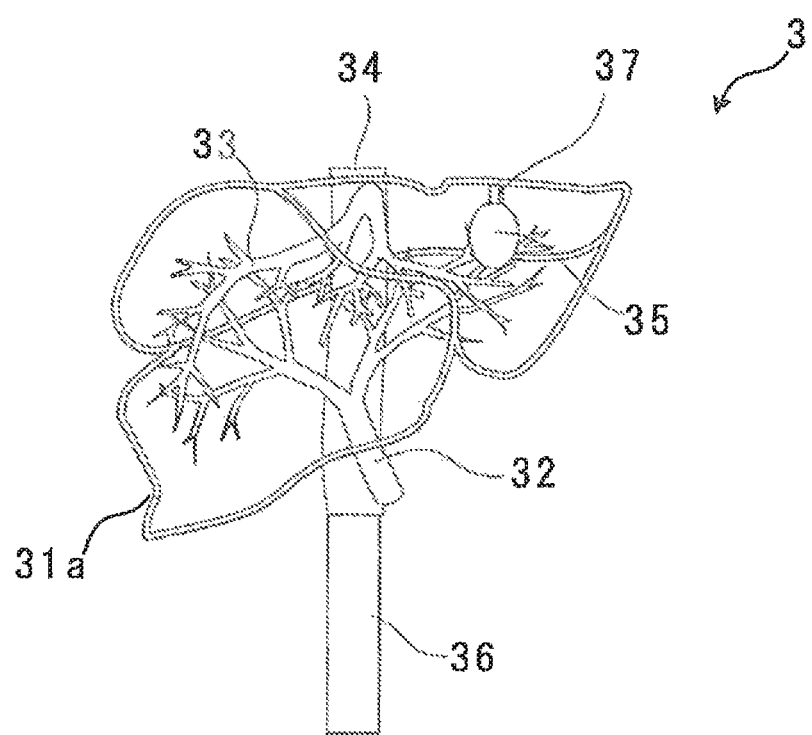
FIG. 4 is a drawing showing a liver model 3.

FIG. 4 is a drawing showing the liver model 3. As shown in the drawing, in the present embodiment, the liver parenchyma 31 is in a hollow frame structure of a frame 31a. The frame 31a traces along at least a part of an outer surface of the liver parenchyma 31 so the shape of the liver parenchyma 31 is represented by the frame 31a. Since the liver parenchyma 31 is in the frame structure, the portal 32, the veins 33, the tumor 35, and the like inside thereof can be observed easily.

Also, this liver model 3 can be handled easily by gripping a gripping part 36 provided at a lower end face of the inferior vena cava 34. Moreover, the tumor 35 is integrated with the liver model 3 by means of a joint part 37 so that the tumor 35 does not fall off. The size of the liver model 3 is approximately half the size of a real liver, although it is not limited thereto.

(3. Three-Dimensional Shape Data for Liver Parenchyma 31, Portal 32, Veins 33, Inferior Vena Cava 34, Tumor 35)

In the present embodiment, when generating three-dimensional shape data for model manufacturing purposes of the liver model 3, the three-dimensional shape data for the liver parenchyma 31, the portal 32, the veins 33, the inferior vena cava 34, the tumor 35, and the like are input into the information processing device 5 in advance as STL (Standard Triangulated Language) data and stored in the storage unit 52 or the like.

These three-dimensional shape data are obtained from DICOM (Digital Imaging and Communications in Medicine) data obtained by scanning a liver of a patient or the like with CT (Computed Tomography), MRI (Magnetic Resonance Imaging), or the like. The methods thereof are commonly known and thus the descriptions thereof are omitted.

Solid lines in FIG. 5 (a) to FIG. 5 (e) are examples of the three-dimensional shape data for the liver parenchyma 31, the portal 32, the veins 33, the inferior vena cava 34, and the tumor 35, respectively. These three-dimensional shape data are determined with a predetermined origin as a base and relative positioning relationships are maintained. Dotted lines in FIG. 5 (b) to FIG. 5 (e) show positions of the liver parenchyma 31 in relation to the portal 32, the veins 33, the inferior vena cava 34, and the tumor 35.

(4. Manufacturing Method for the Liver Model 3)

Figure 6:
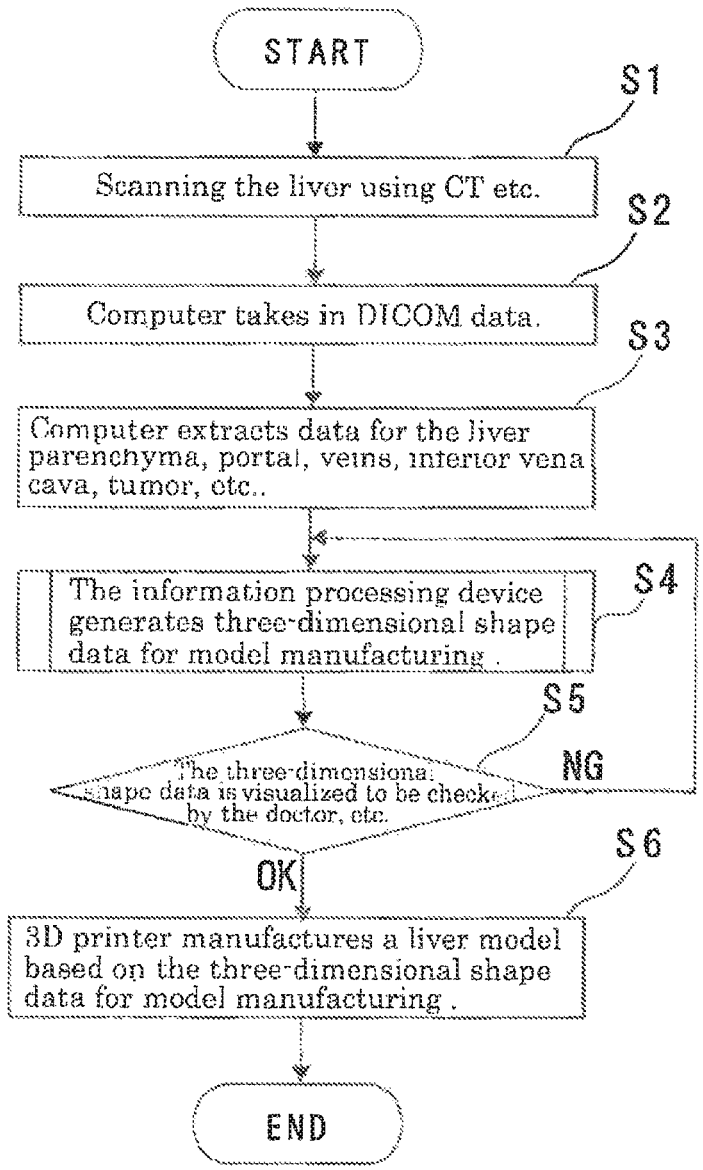
FIG. 6 is a flow chart showing an outline of a manufacturing method for the liver model 3.

Next, a manufacturing method for the liver model 3 will be described. FIG. 6 is a flow chart showing an overview of the manufacturing method for the liver model 3. As shown in the drawing, in the present embodiment, firstly, a liver of a patient or the like is scanned using a CT or the like as mentioned above (S1) and then a computer takes in DICOM data (S2). Then, a doctor or the like points out the liver parenchyma 31, the portal 32, the veins 33, the inferior vena cava 34, and the tumor 35 on the three-dimensional data obtained from the DICOM data and the computer extracts the three-dimensional shape data thereof (S3). Each of the three-dimensional shape data is input into the information processing device 5 and stored in the storage unit 32. Using these three-dimensional shape data, the information processing device 5 generates three-dimensional shape data for model manufacturing purposes of the liver model 3 (S4) and visualize the three-dimensional shape data into an image or the like so as to be checked by the doctor or the like. If the doctor approves (S5; OK), then the 3D printer manufactures the liver model 3 based on the three-dimensional shape data (S6). If not, (S5; NG), the processing flow is back to S4 and the three-dimensional shape data for model manufacturing purposes is re-generated.

(4-1. Generating Three-Dimensional Shape Data for Model Manufacturing Purposes of the Liver Model 3)

Figure 7:
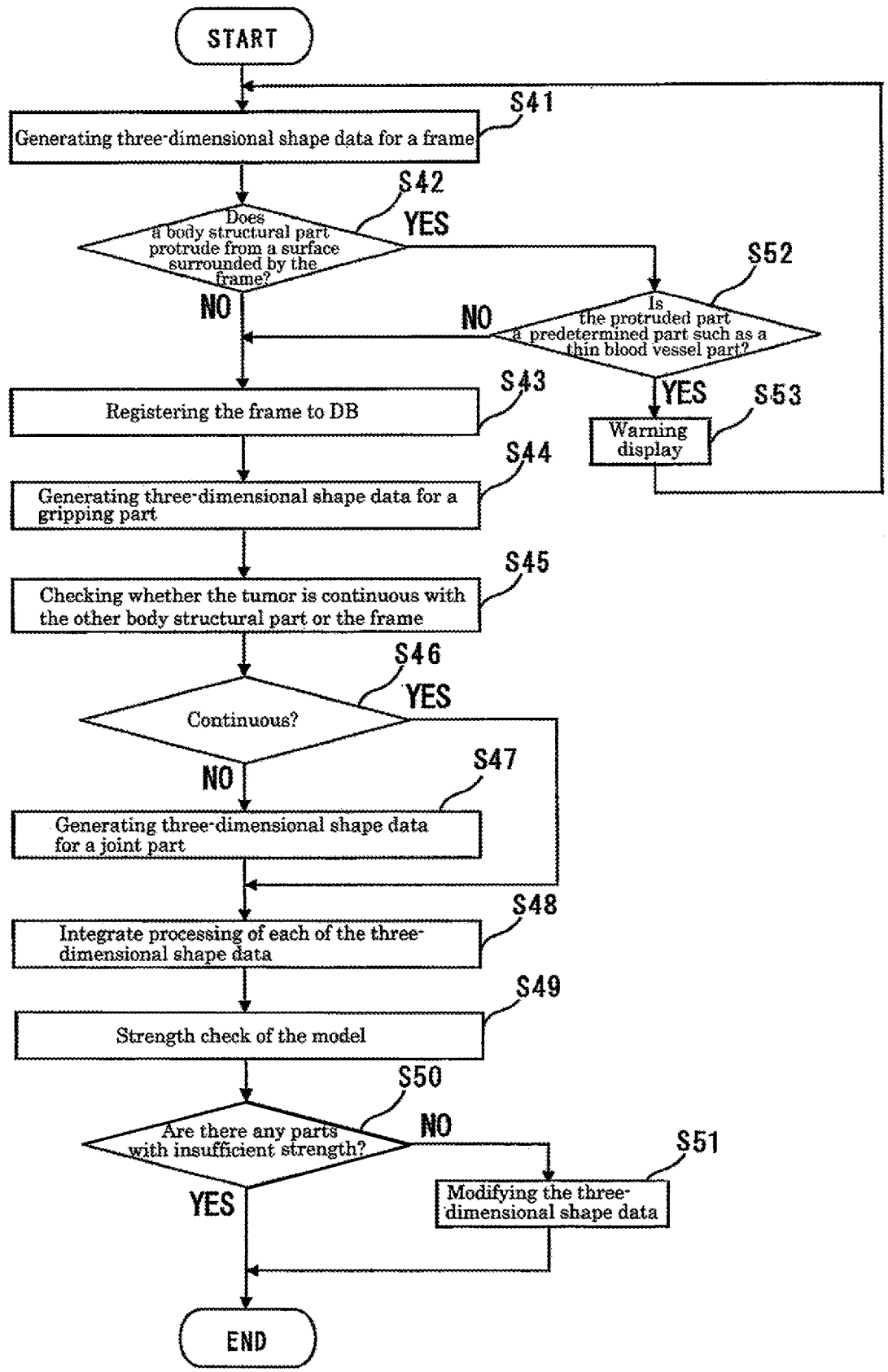
FIG. 7 is a flow chart showing a procedure for generating three-dimensional shape data for the liver model 3.

FIG. 7 is a flow chart showing a process of generating the three-dimensional shape data for model manufacturing purposes of the liver model 3 in S4. The control unit 51 of the information processing device 5 executes each step in the drawing according to user's instruction or input, or automatically executes each step by data calculations.

In S4, the information processing device 5 executes a process of framing the liver parenchyma 31 and generates three-dimensional shape data for the frame 31a (S41).

Figure 8:
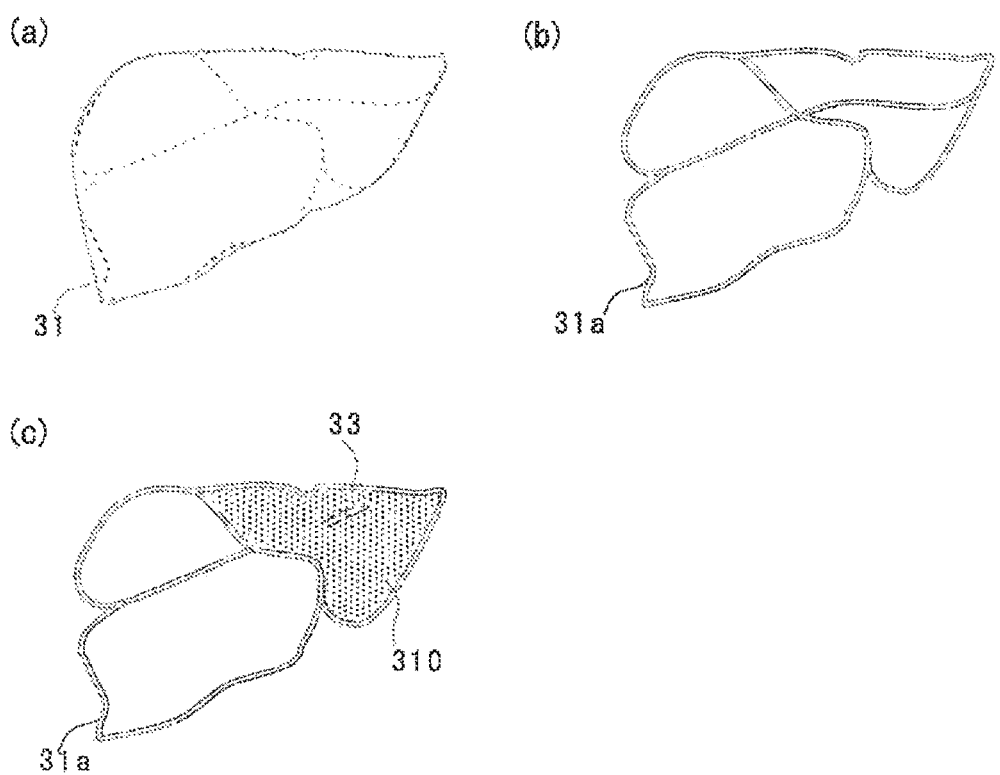
FIG. 8 is a drawing showing a framing process of the liver parenchyma 31.

In S41, frame positions as shown as dotted lines in FIG. 8 (a) are specified by various types of methods, such as tracing along an outer surface of the three-dimensional shape data for the liver parenchyma 31, so that the three-dimensional shape data for the continuous linear frame 31a having a uniform cross sectional shape can be generated as shown in FIG. 8 (b).

Figure 13:
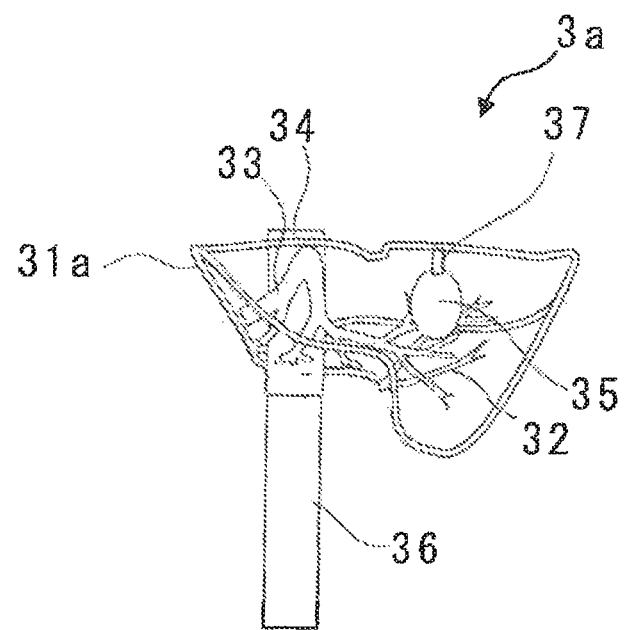

The method for making the frame is not limited thereto, and it is also possible, for example, to specify a predetermined direction and then a front outline of the liver parenchyma 31 viewed from that direction is made into frames. Alternatively, the three-dimensional shape data for the frame 31a can be generated by making the outer surface of the liver parenchyma 31 into a hexagonal-honeycomb structure. Also, since the liver parenchyma 31 includes a plurality of lobule parts, the boundaries of these parts can be made into frames (FIG. 8 (a) is an example in which the boundaries are used as the frames). It is also possible to make one part of the above-mentioned parts into frames and to manufacture a model of a part of the liver parenchyma 31 as shown in FIG. 13, which will be described below.

The frame 31a traces along at least a part of the outer surface of the liver parenchyma 31 and thus the shape of the liver parenchyma 31 can be represented. Furthermore, in addition to such frames as the frame 31a, three-dimensional shape data for linear parts that join between the frames 31a may be generated and used to constitute the three-dimensional shape data for the frames together. This can improve the strength of the frame.

Also, to facilitate distinguishing the frame 31a from the body structuring parts such as the portal 32 and the veins 33, it is possible to make the cross sectional shape of the frame 31a different from that of the body structuring parts such as the portal 32 and the veins 33, or to give depressed or projected shapes such as grooves on the outer surface of the frame 31a. Also, when manufacturing the model, the color of the model material of the frame 31a can be changed from that of the body structuring parts such as the portal 32 and the veins 33. The body structuring parts such as the portal 32 and the veins 33 can be distinguished from each other by changing the colors of the model materials thereof from one another.

Furthermore, the three-dimensional shape data for the frame 31a can be divided into the outer surface and its interior, and when forming by the 3D printer, the outer surface can be formed from a model material having optical transparency whereas the interior can be formed by using a support material so that the color of this support material can help distinguishing the body structuring parts such as the portal 32 and the veins 33 formed of the model material. Alternatively, opposite to the above, the three-dimensional shape data for the body structuring parts such as the portal 32 and the veins 33 can be divided into the outer surfaces and the interiors and, similarly to the above, the outer surface is formed of a model material and the interior is formed of a support material so as to be distinguished from the frame 31a formed of the model material.

In the present embodiment, as shown in FIG. 8 (c), a check on whether a predetermined part of the body structuring parts, such as a thin blood vessel part like a tip of the vein 33 or the like, protrudes from a surface 310 that are surrounded by the frame 31a is carried out. This protrusion check determines whether the body structuring part protrudes from the surface 310 surrounded by the frame 31a, for example, and if so (S42; YES), it is checked whether this protruded part is a predetermined part such as a thin blood vessel part. If such a blood vessel part protrudes from the surface 310, damage like breaking of the blood vessel part may likely occur in handling of the model. Thus, if the protruded part is the predetermined part such as a thin blood vessel part (S52; YES), then a warning is displayed on the display unit 54 or the like of the information processing device 5 (S53), and re-generation of the frame 31a is suggested by designating other frame positions so that such predetermined part does not protrude from the above-mentioned surface 310, or the like. If there are no protrusion of the predetermined part of the body structuring part such as a thin blood vessel part of the vein 33 from the above-mentioned surface 310 (S42; NO or S52; NO), then the frame 31 is appropriate and registered into the DB (database) of the storage unit or the like (S43) so as to be used in the next process of making a frame structure. When automatically generating the three-dimensional shape data for the frame 31a, the above-mentioned checking process can be incorporated so that the three-dimensional shape data for the frame 31a can be generated while making sure that the thin blood part or the like does not protrude from the surface 310 surrounded by the frame 31a. Also, the above-mentioned checking process and the like is one example and it is not limited thereto.

Additionally, in S41, a specific part such as an incised part in operation can be designated and the three-dimensional shape data for the frame 31a can be generated avoiding the specific part. This facilitates viewing of the body structural parts such as the portal 32, veins 33, and the tumor 35 inside the designated part.

Description of the flow chart will be continued. The information processing device 5 generates three-dimensional shape data for the gripping part 36 of the liver model 3 (S44).

Figure 9:
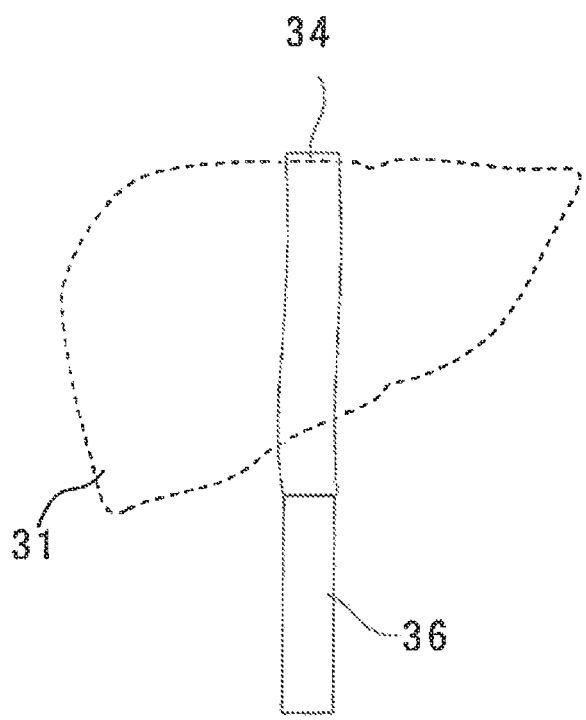
FIG. 9 is a drawing illustrating the generation of three-dimensional shape data for a gripping part 36.

In S44, as shown in FIG. 9, three-dimensional shape data for a column like object extending outward in a vertical direction from a lower end surface of the three-dimensional shape data for the inferior vena cava 34 is generated, for example, to form the gripping part 36. However, the shape of the gripping part 36 is not limited thereto. For example, a hole can be given to the three-dimensional shape data for the gripping part 36 so that a supporting rod on a pedestal of the liver model 3 (not shown in the drawing) can be inserted therein when arranging the liver model 3. It is also possible to give depressed and protruded shapes to the outer surface thereof so that the gripping part 36 can be held easily. Furthermore, the gripping part 36 can also be generated from the three-dimensional shape data for a body structuring part or the like other than the inferior vena cava 34.

The information processing device 5 compares the three-dimensional shape data for the tumor 35 with the three-dimensional shape data for the other body structural parts or the frames 31a and determines whether the tumor 35 is continuous with the other body structural parts or the frames 31a (S45). If so (S46; YES), the process moves on to S48, which will be described below. If not (S46; NO), three-dimensional shape data for the joint part 37 of the tumor 35 is generated (S47).

Figure 10:
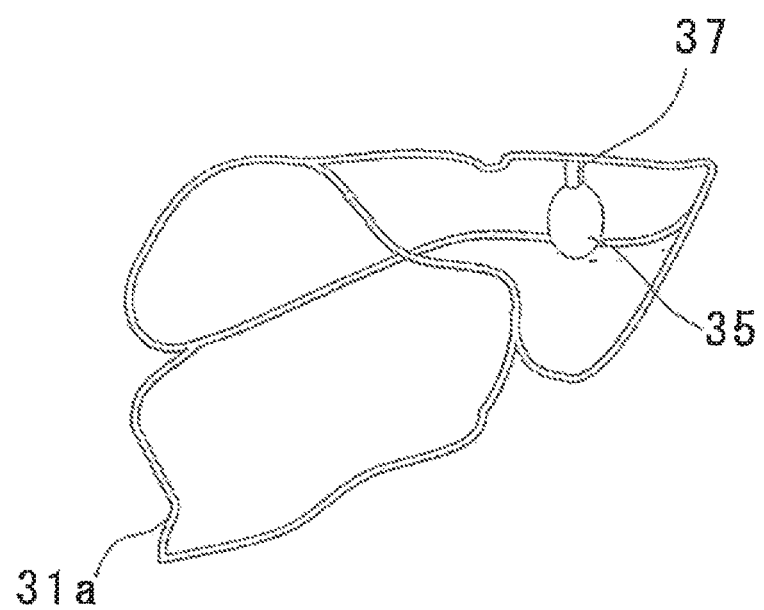
FIG. 10 is a drawing illustrating the generation of three-dimensional shape data for a joint part 37.

FIG. 10 shows the generation of the three-dimensional shape data for the joint part 37 of the tumor 35. In the present embodiment, the three-dimensional shape data for the joint part 37, which joins between the tumor 35 and the subject part (the frame 31a in the example shown in the drawing), is generated at a place where the distance between the tumor 35 and the other body structuring part or the frame 31a is the shortest. However, the position of the joint part 37 is not limited thereto as long as the joint part 37 connects the tumor 35 with the other body structuring part or the frame 31a.

Also, although the joint part 37 is in a rectangular column shape, it is not limited thereto. However, it is preferable that the joint part 37 has a different cross sectional shape from that of the body structural parts such as the portal 32 and the veins 33 to be distinguishable. To realize this, other than making the joint part 37 into a rectangular shape, it is also possible to give depression and protrusion shapes to the outer surface thereof. Alternatively, the color of the model material for the joint part 37 may be changed from that of the body structural parts such as the portal 32 and the veins 33 when manufacturing the model. Also, similarly as above, it is possible to divide the three-dimensional shape data for the joint part 37 into an outer surface and an interior thereof, and the outer surface can be formed from a model material having optical transparency while the interior can be formed by using a support material.

Also, in the present embodiment, the three-dimensional shape data for the parts other than the tumor 35 is continuous and the tumor 35 is connected to the frame 31a with the joint part 37 so as to form a unified model. However, in some cases, the continuous check in S45 can be carried out on the body structural parts other than the tumor 35, such as a thick blood vessel part like the inferior vena cava 34 and thin blood vessel parts such as the vein 33, to check whether the connection thereof with the other body structural parts or the frame 31a, or to check whether the three-dimensional shape data for the frame 31a and each of the body structural parts are continuous as a whole. If discontinuity is found, it is preferable that three-dimensional shape data for a joint part that connects the discontinuous parts is generated as similarly as above.

The information processing device 5 carries out a Boolean operation taking the union of the sets of the three-dimensional shape data generated as above for the frame 31a, the gripping part 36, and the joint part 37, and each three-dimensional shape data for the portal 32, the veins 33, the inferior vena cava 34, and the tumor 35 to carry out an integrated processing (S48) and generate the three-dimensional shape data for model manufacturing purposes of the liver model 3.

Figure 11:
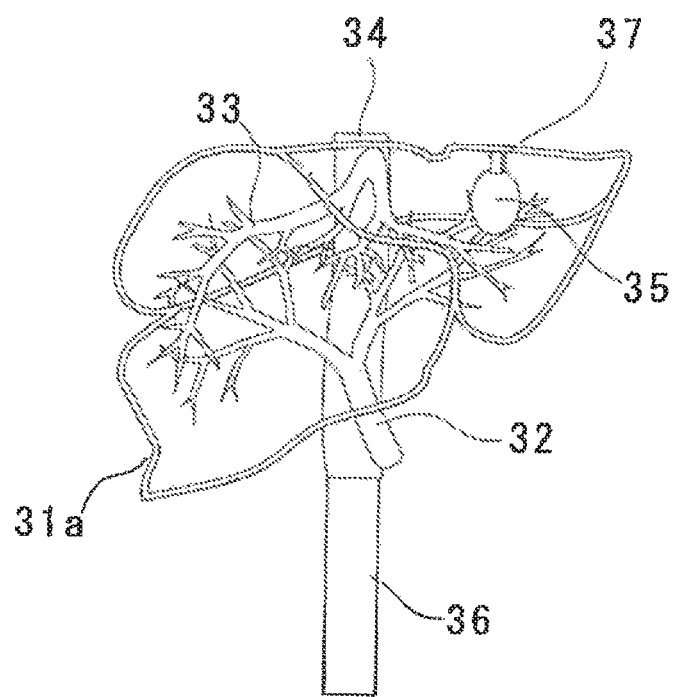
FIG. 11 is a drawing showing the three-dimensional shape data for the liver model 3.

FIG. 11 is a schematic view showing this three-dimensional shape data. Then, in the present embodiment, a strength test of the model is carried out using the three-dimensional shape data (S49). In S49, as a strength test, stress analysis on each part of the three-dimensional shape data is performed, for example, to check whether the parts such as the frame 31a has enough strength to hold the other parts, such as the tumor, or not.

If it is determined that there are no parts with insufficient strength (S50; YES), the process is terminated. If it is determined that there is a part with insufficient strength (S50; NO), the information processing device 5 modifies the three-dimensional shape data (S51). For example, if it is determined that the frame 31a does not have enough strength to hold the tumor 35, the strength thereof is improved by modifications such as thickening the frame 31a or adding three-dimensional shape data for a linear part that connects between the frames 31a for reinforcement. Although the information processing device 5 automatically modifies the three-dimensional shape data in this example, it is also possible to display the parts with insufficient strength on the three-dimensional shape data and accept the user's choice on whether to perform modification by himself or not. If the user chooses to modify it by himself, the information processing device 5 modifies the three-dimensional shape data according to the instruction input by the user.

The three-dimensional shape data generated in this way is visualized to be checked by the doctor or the like and then the 3D printer 7 manufactures the liver model 3 using the three-dimensional shape data in the next process of the flow. It should be noted that the sequential order of the above-mentioned generation and protrusion check of the three-dimensional shape data for the frame 31a (S41 and so on), generation of the three-dimensional shape data for the gripping part 36 (S44), the continuous check of the tumor 35, and the generation of the three-dimensional shape data for the joint part 37 (S45 and S47) may be interchangeable.

(4-2. Manufacture of the Liver Model 3 Using the 3D Printer 7)

Figure 12:
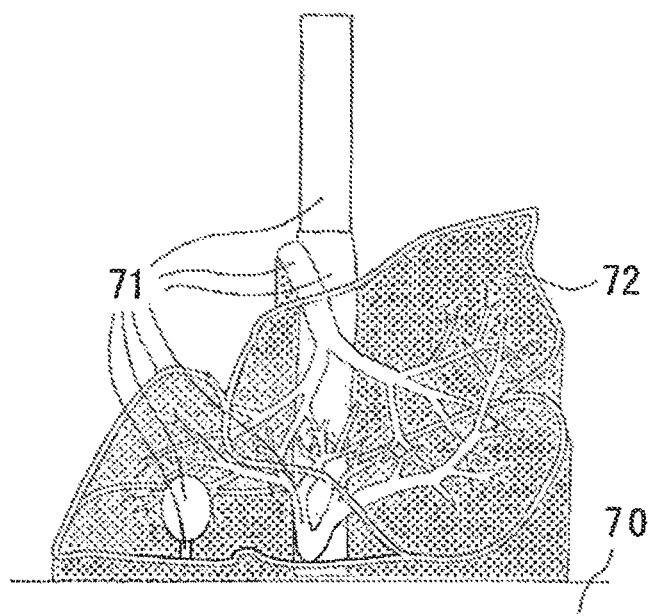
FIG. 12 is a drawing showing a manufacture of the liver model 3 using a 3D printer 7.

FIG. 12 is a drawing showing manufacture of the liver model 3 using the 3D printer 7 in S6 mentioned above (see FIG. 6). In S6, posture of the three-dimensional shape data for model manufacturing purposes of the liver model 3 generated in S4 is determined, and then, as mentioned above, the model material 71 and the support material 72 are applied from an inkjet head (not shown in the drawing) onto a stage 70 according to the slice data obtained from slicing the three-dimensional shape data. The model material 71 is then cured by UV light. These steps are repeated vertically over a plurality of layers.

The model material 71 is applied to the positions of the above-mentioned frame 31a, the gripping part 36, the joint part 37, the portal 32, the veins 33, the inferior vena cava 34 and the tumor 35. The support material 72 is applied to the positions that support the model material 71 from underneath. Finally, when the support material 72 is removed, the liver model 3 shown in FIG. 4 is manufactured.

In this way, three-dimensional shapes that correspond to the three-dimensional shape data for the frame 31a, the gripping part 36, the joint part 37, the portal 32, the veins 33, the inferior vena cava 34 and the tumor 35 are formed from the model material 71 and the manufacture of the liver model 3 is completed.

Another method in which a part of the liver model 3, such as the frame 31a, is manufactured separately from the other parts using the 3D printer 7 and then adhering or mechanically joining thereof together is also possible. In this way, the amount of the support material 72 used can be reduced. In the case of mechanical joining, it is preferable that three-dimensional shape data for that joining part should be generated in above-mentioned S4. Also, different model materials may be used for a part of the liver model 3 and the other parts: for example, the gripping part 36 may be made of a cheaper model material, which may have less strength at the time of curing than the material used for the other parts.

As described above, according to the present embodiment, the liver model 3 can be manufactured easily using an existing 3D printer, and, in this occasion, since the liver parenchyma 31 (the body part), which is a liver body, is in a hollow frame structure, the body structural parts therein, such as the portal 32, the veins 33, and the tumor 35, can be easily observed. Thus, the model is suitable to be used as reference in operation planning or in consultation with patients for informed consent, or to be used for operations, education and so on. Also, the amount of the expensive model material 71 for model manufacturing purposes used is reduced, which reduces the costs, so the present invention can be spread widely not only in the researching field but also in the clinical sites.

Also, joining the body structural part such as the tumor 35 with the other body structural part or the frame 31a by the joint part 37 prevents the body structural part such as the tumor 35 from falling off from the model. Furthermore, providing the gripping part 36 for gripping the model allows the model to be handled easily.

However, the present invention is not limited thereto. For example, in S4, the lower end surface of the three-dimensional shape data for the inferior vena cava 34 or the gripping part 36 mentioned above may be spread into a plate-like shape so that the liver model 3 can stand itself. Also, if necessary, transformation such as thickening blood vessels is possible by thickening the three-dimensional shape data for the body structural parts such as the portal 32 and the veins 33.

Also, the liver model 3 may not be in an integrated body and individual parts may be independently supported. In such a case, the continuous check in S45 can be omitted. Also, if necessary, as shown in FIG. 13, a part of the liver parenchyma 31 can be made into the frame structure to manufacture a liver model 3a for only that part. In this case too, three-dimensional shape data is generated as similarly as described above and then the liver model 3a can be manufactured from the three-dimensional shape data using the 3D printer 7, allowing the model to be downsized.

In the present invention, the body part refers widely to a part of a human or an animal body such as an organ, e.g. a liver, or a muscle and the body structural part refers widely to a structural part, such as a blood vessel and a nerve, associated with the body part. In the present embodiment, a liver is given as an example of the body part and blood vessels, such as the portal 32 and the veins 33, and the tumor are given as examples of the body structural parts for description. It is especially effective to use the present invention for the liver model 3 since there are many opportunities for the liver model 3 to be used in operations and the like and, also, the configuration of blood vessels and tumors thereof is complicated. However, the body part may be a part of a human or an animal and may be a pancreas, for example. In this case, a pancreas parenchyma will be made into a frame structure as similarly as in the present embodiment. Also, the present invention is applicable to internal organs other than a liver and a pancreas, and other organs such as muscles, eyes and so on. Also, it is only necessary that a body structural part is associated with a body part and should include at least a part that is inside the body part in the present invention.

Although the embodiments of the present invention have been described referring to the attached drawings, the technical scope of the present invention is not limited to the embodiments described above. It is obvious that persons skilled in the art can think out various examples of changes or modifications within the scope of the technical idea disclosed in the claims, and it will be understood that they naturally belong to the technical scope of the present invention.

DESCRIPTION OF NOTATIONS

1 . . . manufacturing system
3, 3a . . . liver model
5 . . . information processing device
7 . . . 3D printer
31 . . . liver parenchyma
32 . . . portal
33 . . . vein
34 . . . inferior vena cava
35 . . . tumor
36 . . . gripping part
37 . . . joint part
70 . . . stage
71 . . . model material
72 . . . support material

What is claimed is:

1. A model imitating a body part, comprising:
a frame; and
a body structural part,
both of which are formed from a forming material, wherein:
the frame is continuous linear, and formed along at least a part of an outer surface of the body part; and
at least a part of the body structural part is inside the body part.

2. The model according to claim 1, comprising:
a joint part that joins the body structural part to the other body structural part or the frame.

3. The model according to claim 1, comprising:
a gripping part for gripping the model.

4. The model according to claim 1, wherein:
the body part is a liver.

5. The model according to claim 1, wherein:
the model is manufactured for a part of the body part.

6. A manufacturing system of a model imitating a body part, comprising:
an information processing device; and
a 3D printer, wherein:
the information processing device records three-dimensional shape data for the body part and three-dimensional shape data for a body structural part, at least a part of which is inside the body part, and generates three-dimensional shape data for a continuous linear frame that is formed along at least a part of an outer surface of the body part from the three-dimensional shape data for the body part; and
the 3D printer forms three-dimensional shapes of the frame and the body structural part corresponding to the three-dimensional shape data for the frame and the body structural part respectively from a forming material.

7. The manufacturing system according to claim 6, wherein:
the information processing device generates three-dimensional shape data for a joint part that joins the body structural part and the other body structural part or the frame; and
the 3D printer forms a three-dimensional shape of the joint part corresponding to the three-dimensional shape data for the joint part from a forming material.

8. The manufacturing system according to claim 6, wherein:
the information processing device generates three-dimensional shape data for a gripping part for gripping the model; and
the 3D printer forms a three-dimensional shape of the gripping part corresponding to the three-dimensional shape data for the gripping part from a forming material.

9. The manufacturing system according to claim 6, wherein:
the body part is a liver.

10. An information processing device that generates three-dimensional shape data to be used in manufacturing a model imitating a body part using a 3D printer, wherein:
the information processing device records three-dimensional shape data for the body part; and
the information processing device generates three-dimensional shape data for a continuous linear frame that is formed along at least a part of an outer surface of the body part from the three-dimensional shape data for the body part.

11. The information processing device according to claim 10, wherein:
the information processing device further records three-dimensional shape data for a body structural part, at least a part of which is inside the body part; and
the information processing device generates three-dimensional shape data for a joint part that joins the body structural part to the other body structural part or the frame.

12. The information processing device according to claim 10, wherein:
the information processing device generates three-dimensional shape data for a gripping part for gripping the model.

13. The information processing device according to claim 10, wherein:
the body part is a liver.

14. A manufacturing method for a model imitating a body part using an information processing device and a 3D printer, wherein:
the information processing device, which records three-dimensional shape data for the body part and three-dimensional shape data for a body structural part, at least a part of which is inside the body part, generates three-dimensional shape data for a continuous linear frame that is formed along at least a part of an outer surface of the body part from the three-dimensional shape data for the body part; and
the 3D printer forms three-dimensional shapes of the frame and the body structural part corresponding to the three-dimensional shape data for the frame and the body structural part from a forming material.

15. An information processing method that generates three-dimensional shape data to be used in manufacturing a model imitating a body part using a 3D printer, wherein:
the information processing device generates three-dimensional shape data for a continuous linear frame that is formed along at least a part of an outer surface of the body part from the three-dimensional shape data for the body part.

16. A non-transitory computer readable medium that operates a computer as an information processing device that generates three-dimensional shape data to be used in manufacturing a model imitating a body part using a 3D printer, wherein:
the information processing device generates three-dimensional shape data for a continuous linear frame that is formed along at least a part of an outer surface of the body part from the three-dimensional shape data for the body part.

* * * * *